United States Patent [19]

Tu

[11] Patent Number: 4,865,583

[45] Date of Patent: Sep. 12, 1989

[54] COMBINATION BLOOD SAMPLING AND INTRAVENOUS INFUSION APPARATUS AND METHOD

[76] Inventor: Ho C. Tu, 241 N.E. 199 La., Miami, Fla. 33179

[21] Appl. No.: 185,306

[22] Filed: Apr. 20, 1988

Related U.S. Application Data

[63] Continuation-in-part of Ser. No. 45,589, May 4, 1987, abandoned.

[51] Int. Cl.$^4$ .............................................. A61M 5/00
[52] U.S. Cl. ........................................ 604/53; 604/86; 604/248
[58] Field of Search ...................... 604/83, 4, 9, 30, 32, 604/248, 86, 53

[56] References Cited

U.S. PATENT DOCUMENTS

| | | | |
|---|---|---|---|
| 3,057,350 | 10/1962 | Cowley | 604/248 |
| 3,276,472 | 10/1966 | Jinkens et al. | 604/83 X |
| 3,898,988 | 8/1975 | Morgan | 604/86 |
| 4,219,021 | 8/1980 | Fink | 604/248 X |
| 4,566,480 | 1/1986 | Parham | 604/32 X |
| 4,608,996 | 9/1986 | Brown | 604/32 X |

*Primary Examiner*—Stephen C. Pellegrino

[57] ABSTRACT

Combination intravenous infusion/blood sampling and medication injection apparatus is provided whereby a patient may be administered an intravenous infusion fluid and be subjected to blood sampling or medication injector procedures without the need to make or break any fluid connection in a sealed closed system in order to prevent possible contamination from entering the apparatus and causing injury to the patient. In combination, a three-way valve and a diaphragm sealed blood sampling apparatus is connected to intravenous infusion and catheter tubing and a flushing syringe having sterilized connections is provided. The patient need only be connected to the catheter needle once and by manipulation of the three-way valve in conjucntion with the flushing syringe, the tubing may be purged of the intravenous infusion fluid. A blood sampling syringe or medication containing syringe may thereafter be connected through the self-sealable diaphragm of the blood sampling apparatus to draw a blood sample or to inject medication. Any number of blood samples may be taken or medications injected without the need to further puncture the vein or artery of the patient and in such a manner that a completely sterile environment is maintained. Following use of the combination apparatus, the entire apparatus may be disposed of without the need for subsequent re-use or sterilization.

7 Claims, 2 Drawing Sheets

COMBINATION BLOOD SAMPLING AND INTRAVENOUS INFUSION APPARATUS AND METHOD

CROSS REFERENCE TO RELATED APPLICATIONS

This application is a continuation-in-part of prior U.S. patent application Ser. No. 46,589, filed May 4, 1987, entitled Combination Blood Sampling and Intravenous Infusion Apparatus and Method, by Ho Chung Tu, and now abandoned.

BACKGROUND OF THE INVENTION

1. Field of the Invention

This invention pertains in general to the field of sterilized medical apparatus and in particular to the field of combination intravenous infusion and blood sampling or medication injection apparatus which provides a completely sterile environment for obtaining blood samples from a patient or injecting medication into a patient who is connected to intravenous infusion apparatus.

2. Description of the Prior Art

In recent years in the medical field a great amount of emphasis has been placed upon new and different sterilized procedures whereby the advent of contamination of a patient is either minimized or completely eliminated. The success of such efforts are in a large measure attributable to the ability to mass produce various components made from inexpensive plastic materials. By using such materials, the apparatus in question is completely sterilized and then placed within the sealed sterile container. After use, the apparatus is simply discarded. This overcomes the prior art reusable apparatus which after use must necessarily be resterilized and set aside for later use. During such storage periods the equipment must be maintained within a sterile environment in order to preserve such sterility. Unfortunately, the ability to sterilize and maintain such apparatus in a completely sterile condition prior to re-use is not readily obtainable and contamination of such equipment has caused serious infections in patients. Accordingly, the move to prepackage sterilized and disposable apparatus is extremely beneficial.

One example of still problematic procedures involves a baby patient where blood gas specimens are being drawn in order to monitor oxygen therapy. In this example specimens may be required as often as twenty times a day and for as much as two weeks. In the prior art this routine procedure involved a setup where the arterial umbilical line of the baby is continuously connected to an intravenous solution supply through a three-way valve. The valve allows for disconnection and reconnection of up to three different syringes which are necessary for the blood gas sampling procedure. These disconnections and reconnections involve many steps, each of which increases the risk of contamination of the baby's arterial line. The arterial line opens the entire body of the baby to a possibly contaminated environment. Once bacteria get into the blood stream via the arterial umbilical line, the bacteria travel and multiply in any organ of the body. And, since the bacteria from a hospital environment are usually resistant to antibiotics, the end result could be that the baby dies of infection.

In another example the patient may be receiving intravenous medication through a vein in the patient's arm and it is desirous to obtain a number of blood samples over an extended period of time. In this example similar apparatus is used where a syringe is connectable to a port of a three-way valve. Again, in this routine procedure it is required to disconnect and reconnect a number of syringes to the syringe port in order to draw a blood sample. And, again, there is the distinct possibility of contamination entering the patient's body from the contaminated syringe port of the valve. The contamination can occur from a previously sterile syringe being placed on the patient's bed during the syringe changing operations which is then reconnected to the syringe port. It is because of the relatively large number of steps involved during the procedure that hospital personnel sometimes forget to cover the tips of the disconnected syringes and place them on the patient's bed causing the contamination. Of course, it is possible in the second example to avoid contamination by using one arm for blood sampling and the other arm for injecting the medicinal solution. But, in this event the patient experiences numerous punctures which are obviously undesirable.

Accordingly, it is an object of the present invention to provide medical apparatus whereby a procedure which allows for intravenous infusion of medicinal fluids into a patient and periodic blood sampling from the patient utilizing apparatus which is continuously sterile in a closed system and thereby prevent injury to the patient from contaminated equipment.

Another object of the present invention is to provide medical apparatus whereby the patient may be intravenously infused with a medicinal fluid and where periodic blood samples are obtained from a catheter inserted in an artery.

Another object of the present invention is to provide medical apparatus whereby procedure may be utilized wherein both intravenous infusion and blood sampling of the patient may occur utilizing medical apparatus which is disposable.

The above-stated objects as well as other objects which although not specifically stated, but are intended to be included within the scope of the present invention, are accomplished by the present invention and will become apparent from the hereinafter set forth Detailed Description of the Invention, Drawings, and the claims appended herewith.

SUMMARY OF THE INVENTION

The above objects as well as other objects are accomplished by the present invention which comprises medical apparatus of a disposable type which allows a completely sterilized procedure for either intravenous infusion or blood sampling of a patient in a generally non-sterile environment.

A three-way valve is provided having one port which is connected to a port of a sealed blood sampling apparatus, the outlet of which is connected to a catheter which may be used to be attached to a patient's vein or artery. Another port of the three-way valve is connected to intravenous infusion tubing which may be connected to a source of intravenous medicinal fluid. The remaining port of the three-way valve is connected to a flushing syringe. By manipulation of the three-way valve, the two ports connecting the intravenous fluid with the catheter in the patient's vein or artery may be effectuated and thereby provide for intravenous infusion to the patient. By manipulating the valve to open the catheter and flushing syringe ports, the intravenous infusion is stopped and the fluid within the catheter tubing may be flushed by using the flushing syringe. Thereafter, after all of the intravenous fluid has been flushed from the catheter tubing, and when blood from the patient reaches the flushing syringe the needle of a blood sampling syringe may be applied to the sealed sampling apparatus and an appropriate blood sample may be taken. Following the blood sampling, the three-way valve may be again manipulated to connect the intravenous fluid to the catheter tubing and thus allow a continuation of the intravenous infusion procedure. Any number of blood samples may thereafter be taken at periodic times by utilizing the same procedure as aforedescribed with the combination blood sampling and intravenous solution infusion apparatus being left in place. Upon completion of the combination intravenous infusion/blood sampling procedure which can be as long as two weeks or more, the three-way valve, the sealed blood sampling apparatus, the catheter tubing, the flushing syringe and the intravenous tubing may be removed from the patient and completely discarded. By using such a procedure as above-described, there is no need to disconnect and reconnect the various syringes which in the prior art opened the system to a contaminated environment. Thus, there is no chance of the patient being injured by the normal contamination which is ever present about the bed location of the patient. By making the apparatus of inexpensive plastic or silicon material, the medical apparatus provided by this invention is disposable without the need for subsequent re-use and sterilization. And, because the number of steps involved in the procedure is decreased, the procedure is much more simple and, therefore, less prone to error.

Various other objects, advantages and features of the invention will become apparent to those skilled in the art from the following discussion taken in conjunction with the following drawings, in which:

DESCRIPTION OF THE PREFERRED EMBODIMENTS

Figure 1:
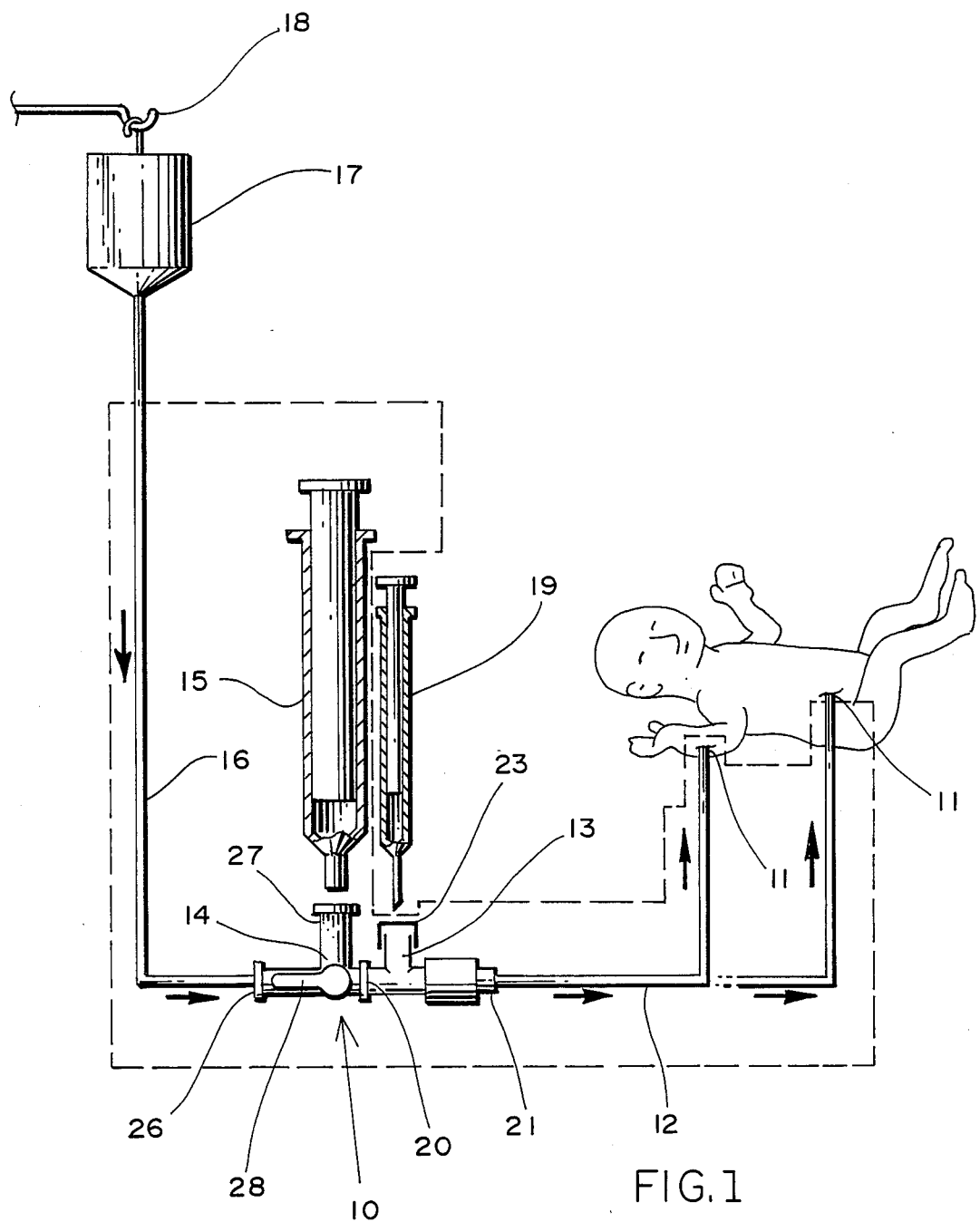
FIG. 1 schematically illustrates the inventive apparatus as applied to a patient's vein or artery or a baby's umbilical line which allows a sterile procedure involving periodic blood sampling in combination with intravenous infusion of a medicinal fluid.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings wherein like characteristics and features of the present invention shown in the various figures are designated by the same reference numerals.

Figure 2:
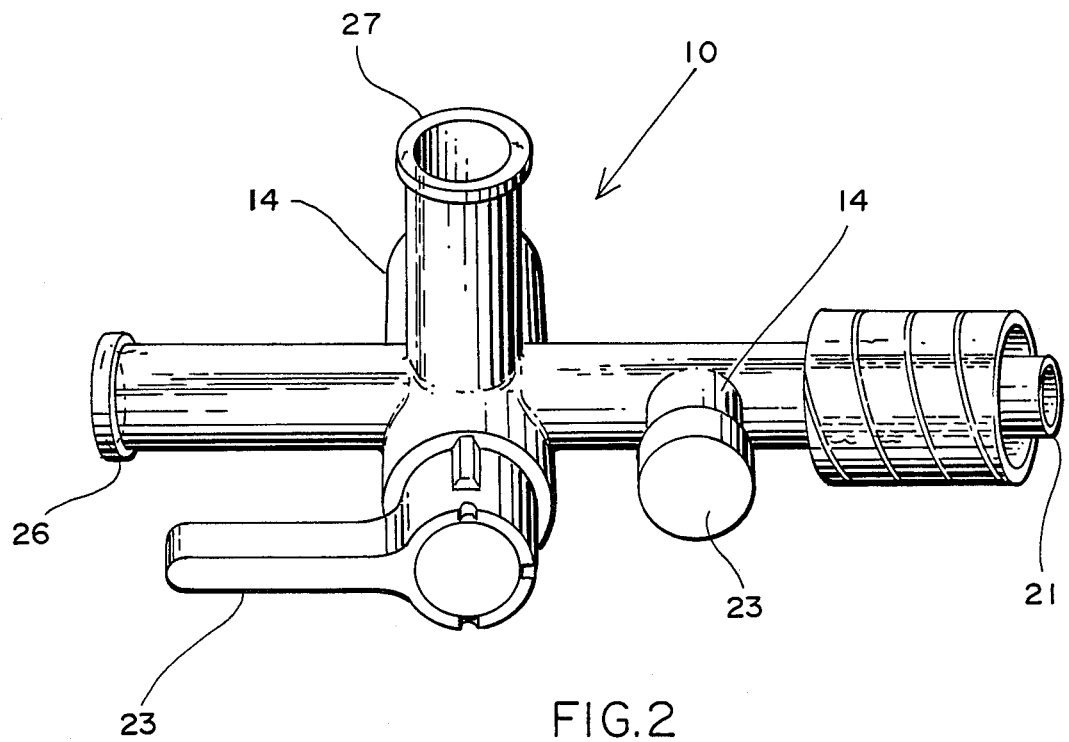
FIG. 2 is an isometric rendering of a combination three-way valve and blood sampling device which may be used with the present invention; and, FIG. 3 is a partial cross-sectional view of the apparatus of FIG. 2 showing the details of the injection or sampling port.

Reference is now made to FIG. 1 of the drawings, which schematically depicts an exemplary embodiment of the present invention. A patient is shown who may comprise an adult or a child having his blood oxygen level continuously being monitored and/or having his blood being sampled on a periodic basis while being administered an intravenous fluid. A catheter 11 is inserted in a vein within his arm or canalized in an umbilical artery at the umbilical tube. The inlet end 12 of the catheter 11 is connected to the outlet port 21 of a sealed blood sampling device 13. Blood sampling device 13 comprises a main body portion having inlet and outlet ports 20 and 21, respectively, connected thereto in addition to a third port 22 which is sealed by a diaphragm 32 made from rubber or other appropriate material. The inlet port 20 of blood sampling device 13 may be directly connected to outlet port 24 or, in the alternative may be connected to an outlet port 24 of a three-way valve 14 by a short length of tubing. The connection of ports 20 and 21 of blood sampling device 13 to tubing 12 and to outlet port 24 or three-way valve 14 is accomplished in a sterile environment at final assembly of the inventive apparatus. It is to be noted that the connections to ports 20 and 21 are not intended to be disconnected at any time after final assembly of the inventive apparatus. Thus, no contamination can enter the inventive apparatus through the connections of these ports. Similarly, the rubber diaphragm 32 across port 22 is of a permanent nature such that no contamination may enter at this location. In the alternative embodiment shown in FIG. 2, the blood sampling device 13 is integrally connected to the three-way valve 14, hence no port connections between items 13 and 14 are required and, therefore, there is no possibility of contamination.

Three-way valve 14 includes three ports: namely, an intravenous infusion port 26, a flushing syringe inlet port 27, and the aforementioned outlet port 24. A valve handle 28 is connected to a rotatable cylinder within three-way valve 14 which allows the connection of either ports 26 and 24 or ports 27 and 24. A flushing syringe 15 is connected to flushing inlet port 27 of three-way valve 14 and may be left in place throughout the procedure when the inventive apparatus is used. In this manner no contamination may enter by way of the connection of flushing syringe 15 to inlet port 27. Flushing syringe 15 may be used as hereinafter described to flush the intravenous infusion fluid from the location of three-way valve 14 to the connection of catheter 11 when it is desired to cease the intravenous fusion and obtain a blood sample.

The intravenous infusion inlet port 26 of three-way valve 14 is connected to intravenous fusion tubing 16 at one end thereof. The other end of intravenous fusion tubing 16 is appropriately connected to a container 17 of appropriate intravenous infusion solution. The container 17 of intravenous infusion solution is appropriately connected to a stand 18 such as is commonly used in an intravenous infusion procedure. All of these connections are made in a normal manner which assures that no contamination occurs.

The apparatus as provided by this invention comprising the intravenous infusion tubing 16, the three-way valve 14, the catheter tubing 12, and the catheter 11, as well as the flushing syringe 15 may all be made from disposable plastic materials which have been sterilized prior to and during the various connections of these components and packaged in the sealed sterile container for use when needed. The sealed container is indicated by the dashed line in FIG. 1 around items 16, 15, 14, 13, 12 and 11. When it is desired to use the inventive apparatus, the sealed container is opened at the location of the patient and appropriately attached to the patient and a container of intravenous infusion fluid. The length of catheter tubing 12 is such that the blood sampling device 13, the three-way valve 14, and the flushing syringe 15 may be placed an appropriate distance away from the patient such that movement of the patient does not interfere with said apparatus.

When it is desired to obtain a blood sample from the patient, the lever 28 of three-way valve 14 is manipulated to connect ports 27 and 24 and thereby close port 26. Then, the flushing syringe 15 is operated to draw all of the intravenous solution in catheter tubing 12 and the entrance to syringe 15 with blood from the patient. This procedure will also cause the internal passages of blood sampling device 13 to fill with the patient's blood. A blood sampling syringe 19 is then applied to the diaphragm 32 of the blood sampling device 13 thereby piercing the diaphragm 32 by the needle of syringe 19 and connecting the blood sampling syringe 19 thereto. Then, a blood sample may be taken from the patient by activating the plunger of blood sampling syringe 19. When a desired amount of blood has been withdrawn from the patient, blood sampling syringe 19 may be removed from the diaphragm 32 of the blood sampling device 13. Because of the nature of diaphragm 32, the sealed opening across port 22 is reestablished when the needle of blood sampling syringe 19 is removed from diaphragm 32. After removal of syringe 19, the plunger of syringe 15 is pushed down thereby pushing the blood within syringe 15 and catheter tubing 12 back into the patient. Flushing syringe 15 is then in a position for re-use when another blood sample is to be taken. Lever 28 of valve 14 is then moved to reconnect ports 24 and 26 and close port 27. This procedure reconnects the container 17 of infusion fluid to the patient to allow continuation of the intravenous infusion. At any time thereafter and for as many times as desired, the aforestated procedure may be repeated in order to obtain additional blood samples from the patient. When the combination intravenous infusion and blood sampling procedure is completed, the catheter 11 may be removed from the patient and the intravenous infusion tubing 16 may be removed from the intravenous infusion container 17 and discarded in an appropriate manner.

It is to be noted that all of the operations performed during the alternative intravenous infusion and blood sampling procedures are accomplished in a completely sterilized manner.

The inventive apparatus may also be used to inject medication into the patient. For this procedure flushing syringe 15 may be filled with a solution of normal saline which is then used to flush the catheter tubing 12 with the saline solution. Then, a syringe 19, filled with a predetermined medication, is applied to diaphragm 32. Activation of the plunger of syringe 19 pushes the medication through catheter 11 and into the patient. Syringe 14 may then be removed from device 13 and flushing syringe 15 is further used to push the medication in catheter tubing 12 into the patient. Valve 14 is then set between ports 24 and 26 whereupon the intravenous solution infusion is reestablished into the patient. Again, a completely sterile procedure is effectuated.

Figure 3:
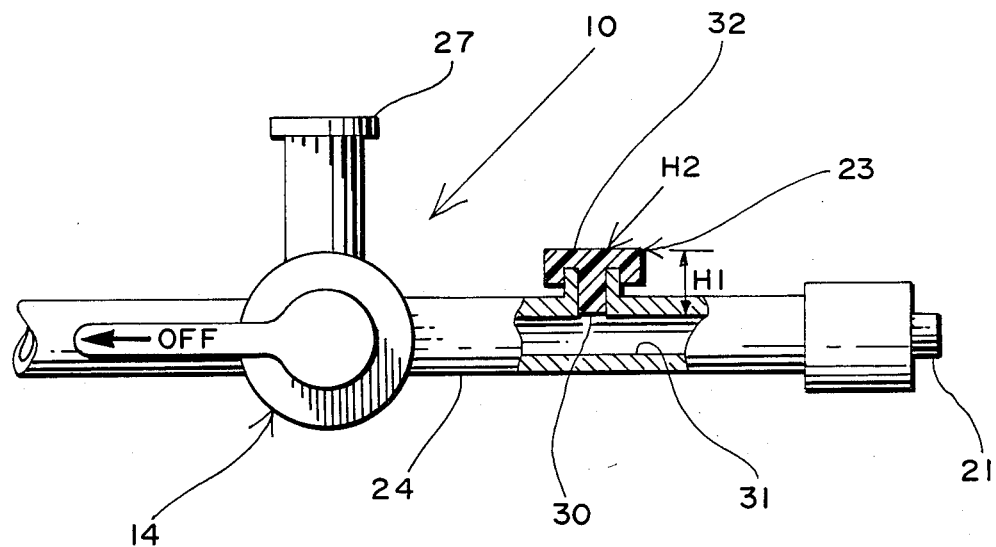

Reference is now made to FIG. 3, of the drawings wherein another preferred embodiment of the invention is shown. In this embodiment, a single unit comprising a three-way valve and an injection/sampling site is utilized. There is no breakable connection between the injection/sampling side and the outlet port 24 of the three-way valve 14. A straight length of non-flexible or rigid tubing 30 connects outlet port 24 of valve 14 to injection/sampling site 23. The use of non-flexible or rigid tubing 30 provides a degree of rigidity to the inventive apparatus generally designed by the number 10.

The rigidity of the inventive apparatus 9 allows the attending physician or the person drawing the blood sample from the patent to easily manipulate the various syringes 15 and 19 and the handle 28 of three-way valve 14. A flexible connection between injection/sampling site 13 and the outlet port 24 of valve 14 may result in a degree of difficulty in manipulating valve 14 and syringes 15 and 19.

Injection/sampling site 23, in the embodiment of FIG. 3 substantially eliminates any air between the rubber stopper or diaphragm 32 and the internal diameter 31 of the inventive device 10. Thus, when a flushing syringe 15 is used to flush the lines between the flushing syringe and the patent, no air is drawn into flushing syringe 15. Consequently, when the fluid within flushing syringe 15 is re-injected back into the patient, no air is allowed to be injected contemporaneously along with the fluid in syringe 15. In order to accomplish this important objective, the overall height $H_1$ of injection/sampling site 23 is made very short and substantially equal to the height of $H_2$ of the rubber diaphragm 32. More importantly, the bottom or lower surface 30 of rubber diaphragm 32 is made substantially flush with the internal diametrical surface 31 of the inventive apparatus 10. In other words, the inventive apparatus 10 eliminates an air pocket between the injection/sampling site 23 and the fluid within the apparatus 10 which connects lines 12 and 16.

In the use of the inventive apparatus for injecting a medicine, the flushing syringe is filled with a saline fluid.

While the invention has been described, disclosed, illustrated and shown in certain terms or certain embodiments or modifications which is has assumed in practice, the scope of the invention is not intended to be nor should it be deemed to be limited thereby and such other modifications or embodiments as may be suggested by the teachings herein are particularly reserved especially as they fall within the breadth and scope of the claims here appended.

I claim as my Invention:

1. In combination, apparatus adapted to supply an intravenous solution to a patient, to allow periodic blood sampling and to allow periodic administering of liquid medicine, comprising a three-way valve having an intravenous fluid infusion port, a flushing syringe port and an outlet line a blood sampling or medical fluid injection site means connected to said outlet line of the three-way valve and in flow communication therewith for alternatively sampling a patient's blood or injecting a liquid medicine into said patient said site means connection to said outlet line of the three-way valve comprising a rigid connection, said site means being integrally connected to said three-way valve and comprising an opening having a diaphragm extending thereacross and sealingly attached thereto.

2. The apparatus of claim 1, wherein said site means and comprising said diaphragm being of a height whereby a bottom surface thereof is substantially aligned with an internal diametrical surface to which said opening is connects, said diaphragm being adapted to be pierced by a needle of a syringe and resealed when the needle is withdrawn therefrom.

3. In combination, apparatus adapted to supply an intravenous solution to a patient, to allow periodic blood sampling and to allow periodic administering of liquid medicine, comprising a three-way valve having an intravenous fluid infusion port, a flushing syringe port and an outlet line a blood sampling medical fluid injection site means connected to said outlet line of the three-way valve for alternatively sampling a patient's blood or injecting a liquid medicine into said patient said site means connection to said outlet line of the three-way valve comprising a rigid connection and said site means being integrally connected to said three-way valve said site means comprising an opening having a diaphragm extending thereacross and sealingly attached thereto, said diaphragm being of a height whereby a bottom surface thereof is substantially aligned with an internal diametrical surface to which said opening is connected.

4. The apparatus of claim 3, including a flushing syringe connected to said flushing syringe port of the three-way valve.

5. The apparatus of claim 3, including a sealed container in which said apparatus is encapsulated.

6. A method for taking a sample of a patient's blood while the patient is being administered an intravenous solution comprising the steps of inserting a catheter into a patient, said catheter being connected by flexible tubing to a combination three-way valve having a blood sampling site rigidly connected downstream thereto, said sampling site having a flexible diaphragm with an inner end being substantially in alignment with an inner diameter of an outlet port of the three-way valve, the three-way valve having an inlet port connected to a supply of intravenous fluid and a third port connected to a flushing syringe operating the catheter apparatus such that the intravenous fluid is being administered to the patient shutting off the flow from the intravenous fluid supply operating the flushing syringe drawing into the flushing syringe all the intravenous fluid from the patient to the third port of the three-way valve until such time as the patient's blood is being drawn into the flushing syringe inserting a blood sampling into the blood sampling site and drawing a blood sample withdrawing the blood sampling syringe from the blood sampling site re-operating the flushing syringe in a reverse direction so as to cause the blood and intravenous fluid therein to fill the line between the third port of the three-way valve and the patient, then opening the three-way valve to continue administering the intravenous fluid.

7. A method for injecting a medicinal fluid into a patient when the patient is being administered an intravenous fluid comprising the steps of inserting a catheter into a patient, said catheter being connected by a flexible tubing to a combination three-way valve having an injection site rigidly connected downstream thereto, an injection site having a flexible diaphragm with an inner end being substantially in alignment with an inner diameter of an outlet port of the three-way valve, an inlet port of the three-way valve being connected to a supply of intravenous fluid, and a third port of the three-way valve being connected to a flushing syringe filled with a saline fluid operating the catheter apparatus such that the intravenous fluid is being administered to the patient shutting off the flow from the intravenous fluid supply operating the flushing syringe so as to inject some of the saline fluid in the flushing syringe from the third port of the three-way valve into the patient inserting a syringe filled with a medicinal fluid into the injection site operating the syringe filled with medicinal fluid until the same is injected into the patient and into the line from the patient to the injection site removing the injection syringe from the injection site, and opening the three-way valve so as to continue administering the intravenous fluid to the patient.

* * * * *